United States Patent
Noguchi (10) Patent No.: US 11,547,540 B2
(45) Date of Patent: Jan. 10, 2023

(54) DEVICE FOR ANALYZING OCCLUSION PRESSURE, PROGRAM FOR ANALYZING OCCLUSION PRESSURE, AND METHOD FOR ANALYZING OCCLUSION PRESSURE

(71) Applicant: GC CORPORATION, Shizuoka (JP)

(72) Inventor: Yukie Noguchi, Tokyo (JP)

(73) Assignee: GC CORPORATION, Shizuoka (JP)

( * ) Notice: Subject to any disclaimer, the term of this patent is extended or adjusted under 35 U.S.C. 154(b) by 386 days.

(21) Appl. No.: 16/647,274

(22) PCT Filed: May 17, 2018

(86) PCT No.: PCT/JP2018/019163
§ 371 (c)(1),
(2) Date: Mar. 13, 2020

(87) PCT Pub. No.: WO2019/053949
PCT Pub. Date: Mar. 21, 2019

(65) Prior Publication Data
US 2020/0205953 A1  Jul. 2, 2020

(30) Foreign Application Priority Data

Sep. 14, 2017 (JP) .............................. JP2017-176662

(51) Int. Cl.
*G16H 50/50* (2018.01)
*A61C 19/05* (2006.01)

(52) U.S. Cl.
CPC ............. *A61C 19/05* (2013.01); *G16H 50/50* (2018.01)

(58) Field of Classification Search
None
See application file for complete search history.

(56) References Cited

U.S. PATENT DOCUMENTS 5,458,487 A * 10/1995 Komatsu .............. A61C 9/0053
600/590
2006/0127848 A1 * 6/2006 Sogo ...................... A61C 1/084
433/173
(Continued)

FOREIGN PATENT DOCUMENTS

EP 2564809 A1 3/2013
JP 05-317342 A 12/1993
(Continued)

OTHER PUBLICATIONS

International Search Report for PCT/JP2018/019163, dated Aug. 21, 2018.

*Primary Examiner* — Sultana M Zalalee
(74) *Attorney, Agent, or Firm* — Sughrue Mion, PLLC (57) ABSTRACT

An object is to provide a device for analyzing occlusion pressure with which it is possible to measure occlusion pressure with a high positional accuracy by using data obtained by versatile methods, including an operation device, wherein the operation device calculates a formula of a first dental arch based on an occlusion pressure data, calculates a formula of a second dental arch based on an occlusal contact positional data, calculates a transformation matrix that approximates the formula of the first dental arch to the formula of the second dental arch, carries out an operation to transform positional information included in the occlusion pressure data to a new positional information with the transformation matrix, and outputs an occlusion pressure data including the new positional information.

3 Claims, 4 Drawing Sheets

(56) References Cited

U.S. PATENT DOCUMENTS

| | | | |
|---|---|---|---|
| 2013/0052609 A1* | 2/2013 | Kume | A61C 19/05 |
| | | | 433/71 |
| 2015/0142400 A1* | 5/2015 | Matov | G06F 30/20 |
| | | | 345/420 |
| 2015/0305669 A1 | 10/2015 | Hultgren | |
| 2016/0302901 A1* | 10/2016 | Brel | G01L 1/205 |
| 2019/0298502 A1* | 10/2019 | Szczerbaniewicz | |
| | | | A61C 9/0006 |

FOREIGN PATENT DOCUMENTS

| | | |
|---|---|---|
| JP | 06-125927 A | 5/1994 |
| JP | 06-277240 A | 10/1994 |
| JP | 2005279094 A | 10/2005 |

* cited by examiner

DEVICE FOR ANALYZING OCCLUSION PRESSURE, PROGRAM FOR ANALYZING OCCLUSION PRESSURE, AND METHOD FOR ANALYZING OCCLUSION PRESSURE

CROSS REFERENCE TO RELATED APPLICATIONS

This application is a National Stage of International Application No. PCT/JP2018/019163 filed May 17, 2018, claiming priority based on Japanese Patent Application No. 2017-176662 filed Sep. 14, 2017.

FIELD

The present invention relates to devices for analyzing occlusion pressure at upper and lower rows of teeth in occlusal contact, programs for analyzing occlusion pressure, and a method for analyzing occlusion pressure.

BACKGROUND

As a means for measuring occlusion pressure, pressure sensitive papers (pressure sensitive sheets) are known. A subject bites a pressure sensitive paper, then the paper is strongly pressed at occlusal contacting points of upper and lower rows of teeth, which brings visual changes of the paper. Depending on the kind of the pressure sensitive paper, the changes in size of occlusion pressure (contact pressure) may appear as gradation or variation of color. In this way, occlusion pressure at upper and lower rows of teeth may be found out by means of a pressure sensitive paper.

With a pressure sensitive paper, the changes appear at the points where occlusal contact is made according to occlusion pressure, which makes it possible to identify the locations of occlusal contact to some extent. However, since the surfaces of teeth are three-dimensional having complex concavity and convexity, the pressure sensitive paper changes its shape three-dimensionally along the concavity and convexity of the teeth when bitten. After that, the pressure sensitive paper is taken out from the mouth, and when occlusion pressure is analyzed, the paper whose shape is modified is smoothed out to have planar shape (two-dimensional shape) as much as possible. Accordingly, the pressure sensitive paper in analysis has a different shape from the shape in occlusion. Thus, the actual position of row of teeth and the biting points on the pressure sensitive paper are different, and there is a problem with pressure sensitive papers that the information of the locations of occlusal contact does not correspond to the actual positions.

Conventional analysis and measurement of occlusion pressure include a lot of experimental factors of dentist, or use techniques such as Patent Literatures 1 to 3 in view of reducing such experimental factors.

The technique described in Patent Literature 1 utilizes a special equipment using a pressure sensitive sheet and a wax in combination.

In the technique described in Patent Literature 2, occlusion pressure is shown to a figure made with modification of a normal row shape of teeth depending on patient.

The technique described in Patent Literature 3 uses a sensor to detect the row shape of teeth and a sensor to detect occlusion pressure.

CITATION LIST

Patent Literature

Patent Literature 1: JP H06-125927 A
Patent Literature 2: JP H05-317342 A
Patent Literature 3: JP H06-277240 A

SUMMARY

Technical Problem

However, with the experimental methods by dentists, accurate correspondences are not always made.

With the technique described in Patent Literature 1, there was a possibility that the actual state of occlusal contact is not recreated since a thick wax is intervenient in a measurement of occlusion pressure. In this technique as well, the pressure sensitive sheet is smoothed two-dimensionally as described above when measured, with which the problem regarding accurate position remains. In addition, the procedures for analysis (including program) tend to be complex with this technique.

With the technique described in Patent Literature 2, the normal row shape of teeth needs to be modified depending on patient, which is troublesome. In addition, there is also a problem regarding accurate position since the positioning of the row shape of teeth and pressure distribution is dependent on practitioner and the pressure distribution itself measured with the sheet is not modified.

The technique described in Patent Literature 3 also has a problem regarding accurate position described above since a sheet is used for detection of occlusion pressure.

Considering the above problems, an object of the present invention is to provide a device for analyzing occlusion pressure which makes it possible to measure occlusion pressure with a high positional accuracy by means of data obtained by versatile methods, a program for analyzing occlusion pressure which realizes the same measurement, and a method for analyzing occlusion pressure.

Solution to Problem

Hereinafter the present invention will be described.

One aspect of the present invention is a device for analyzing occlusion pressure that corrects occlusion pressure distribution, including an operation device, wherein the operation device calculates a formula of a first dental arch based on an occlusion pressure data, calculates a formula of a second dental arch based on an occlusal contact positional data, calculates a transformation matrix that approximates the formula of the first dental arch to the formula of the second dental arch, carries out an operation to transform positional information included in the occlusion pressure data to a new positional information with the transformation matrix, and outputs an occlusion pressure data including the new positional information.

Another aspect of the present invention is a program for analyzing occlusion pressure including: a step of calculating a formula of a first dental arch based on an occlusion pressure data; a step of calculating a formula of a second dental arch based on an occlusal contact positional data; a step of calculating a transformation matrix that approximates the formula of the first dental arch to the formula of the second dental arch; and a step of transforming positional information included in the occlusion pressure data to a new positional information with the transformation matrix.

Another aspect of the present invention is a method for analyzing occlusion pressure including: a step of calculating a formula of a first dental arch based on an occlusion pressure data; a step of calculating a formula of a second dental arch based on an occlusal contact positional data; a step of calculating a transformation matrix that approximates the formula of the first dental arch to the formula of the second dental arch; and a step of transforming positional information included in the occlusion pressure data to a new positional information with the transformation matrix.

Advantageous Effects of Invention

According to the present invention, it is possible to identify the positions where occlusion pressure is made using data from information obtained by versatile methods, regardless of the obtainment methods of occlusion pressure and information of occlusal contact positions which are sources of data. In addition, it becomes also possible to measure occlusion pressure at a position with high accuracy based on the analysis results.

DETAILED DESCRIPTION OF EMBODIMENTS

Figure 1:
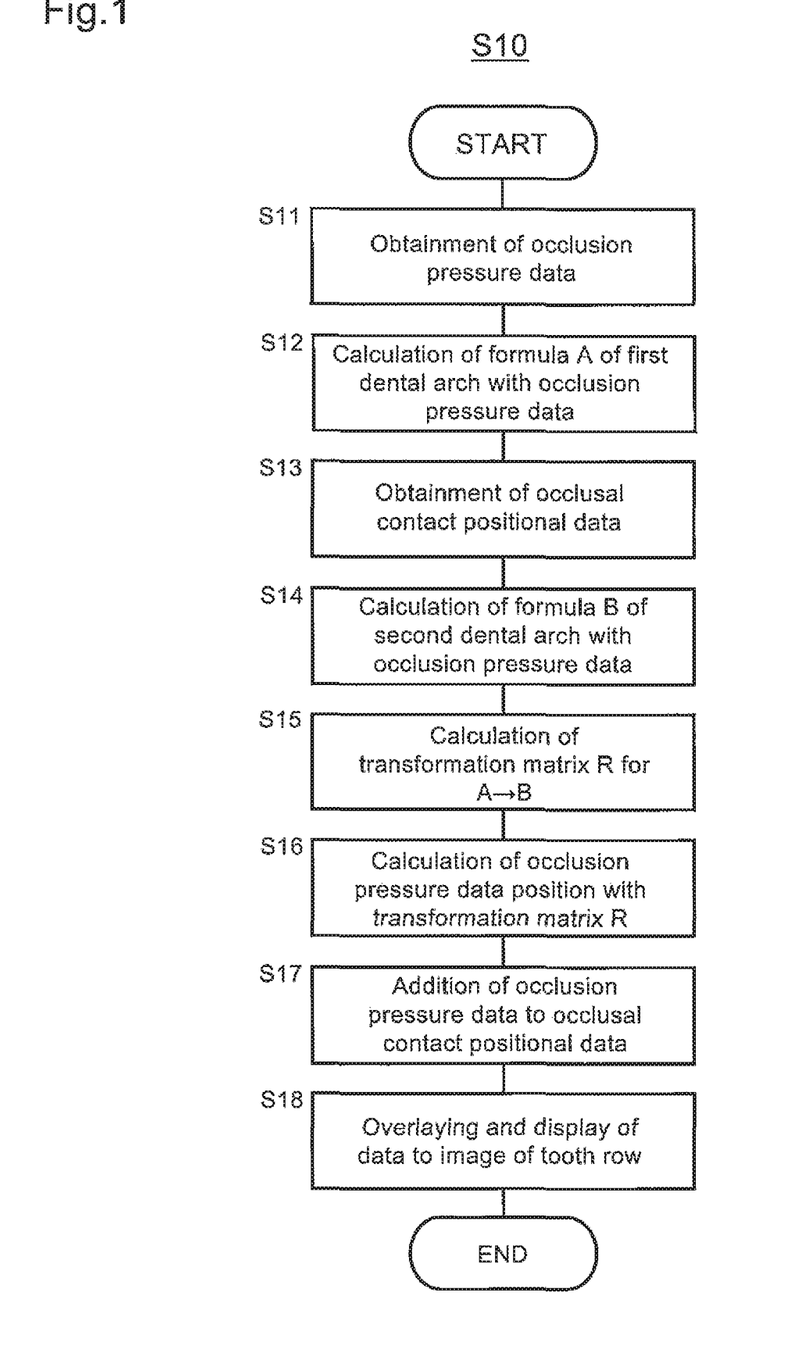
FIG. 1 is a view to explain a flow of an occlusion pressure analysis method S10.

FIG. 1 shows a flow of an occlusion pressure analysis method S10 according to one embodiment. As seen from FIG. 1, the occlusion pressure analysis method S10 includes the steps S11 to S18. Each step is explained below.

The step S11 is to obtain occlusion pressure data. That is, data of two-dimensional positional information (X, Y) and data of occlusion pressure information ($P_{XY}$), of occlusion pressure distributions from the means of detecting occlusion pressure including occlusion pressure distribution information, are obtained.

Here, the means of detecting occlusion pressure is not particularly limited. Examples thereof may include a pressure sensitive paper (pressure sensitive sheet) and a pressure sensitive sensor that detects the positions of occlusal contact with changes of electric properties. Among them, a pressure sensitive paper, which is more versatile than the others and can display occlusion pressure easily, is preferable.

The method for obtaining X, Y, and $P_{XY}$ from the means of detecting occlusion pressure is not particularly limited. When the means of detecting occlusion pressure is a pressure sensitive paper, examples of the method may include a scanner or camera to read in colors and gradations present on the pressure sensitive paper. If the means of detecting occlusion pressure is a pressure sensitive sensor, examples of the method may include a device to measure electrical properties (voltage, current, resistance value, or variation of them) corresponding to occlusion pressure.

Figure 2A:
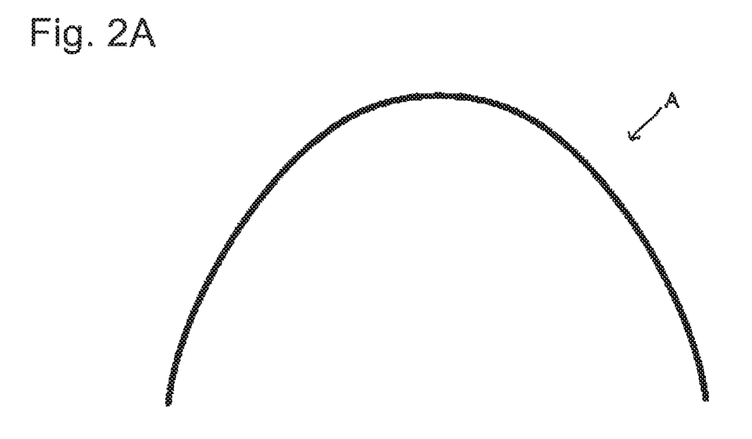
FIGS. 2A and 2B include views schematically showing a curve obtained with the formula A of a first dental arch (FIG. 2A) and a curve obtained with the formula B of a second dental arch (FIG. 2B).

The step S12 is to calculate a formula A of a dental arch (formula A of a first dental arch) with occlusion pressure data as shown in FIG. 2A, from the information data of occlusion pressure generation points (X, Y) among the occlusion pressure data obtained by the step S11.

The calculation of the formula A can be made by regression analysis with the distribution of the occlusion pressure generation points included in the occlusion pressure data. Examples of the regression analysis include least square method.

A more specific example of the calculation is as follows.

The data in which the occlusion pressure ($P_{XY}$) is no less than $P_0$, which is a predetermined threshold value, is extracted, and a regression analysis for the positional information data of the extracted data (X, Y) is carried out, to obtain the following formula of quadratic curve.

Quadratic curve:

$$A_1X^2+A_2XY+A_3Y^2+A_4X+A_5Y+A_6=0$$

Here, X and Y are variable numbers and $A_1$ to $A_6$ are coefficients obtained by the regression analysis.

The threshold value $P_0$ may be appropriately determined in view of the performance of the means of detecting occlusion pressure and securing the numbers of data enough to obtain the formula of the quadratic curve.

In addition, the above-described formula of quadratic curve may be a formula of parabola in which rotation is controlled or a formula of ellipse, in view of easy analysis. They are specifically as follows. $B_1$ to $B_3$ and $C_1$ to $C_5$ in the formulas are coefficients obtained by the regression analysis.

Parabola:

$$Y=B_1X^2+B_2X+B_3$$

Ellipse:

$$C_1X^2+C_2X+C_3Y^2+C_4Y+C_5=0$$

This parabola has an axis parallel to Y axis, and the ellipse has an axis parallel to X axis and Y axis. Therefore, it is possible to make the calculation easy by reducing the coefficients to be obtained.

In addition, in view of easy analysis, not all of the information data of occlusion pressure generation points of no less than the threshold value $P_0$, but only a position taking the largest value of each occlusion pressure area that can be extracted at the threshold value $P_0$, (the area where occlusion pressure generation points connect to each other to be a mass so that an area is formed) or only the data of barycentric position etc. of this area may be used for the regression analysis.

The step 13 is to obtain occlusal contact positional data. That is, it is a step to obtain two-dimensional positional information (x, y) or three-dimensional positional information (x, y, z) where occlusal contact positional distribution is emerged.

Here, the sources of the information where the occlusal contact positional distribution is emerged are not particularly limited, and the following sources may be exemplified.

An impression of oral cavity, or two-dimensional images (pictures, scanner images, etc.) of wax taken when occlusion is made in which occlusal contact positions are shown A picture of oral cavity in which occlusal contact positions are shown A two-dimensional image (picture, scanner image, etc.) of a model of row of teeth (plaster model etc.) in which occlusal contact positions are shown Shape data of three-dimensional scan of an oral cavity in which occlusal contact positions are shown Shape data of three-dimensional scan of a model of row of teeth (plaster model etc.) in which occlusion contact positions are shown Here, the method for showing occlusal contact positions in each picture and data is not particularly limited. For example, the positions in an impression of oral cavity and bitten wax may be identified by shape measurement or light transmission measurement on the portions where became thin by occlusion. The positions in an oral cavity and a model of row of teeth may be identified by image processing with marking of occlusal contact points with a biting paper etc., or with a pressure sensitive paper to which the function of biting paper is added.

As explained above, in the occlusion pressure analysis method S10, the models, pictures, and data used in another treatment and the like may be used as the method for obtaining the occlusal contact positional data, with which general versatility may be increased.

It is preferred that the occlusal contact positional data be obtained from the direction of the normal line of the occlusal plane. This makes it possible to obtain a quadratic curve comparatively similar to the shape of occlusion pressure data, and to increase the correction accuracy.

When pictures etc. obtained from a position different from the direction of the normal line (such as a direction oblique to the normal direction having an angle), the positional information may be identified three-dimensionally (three-dimensional coordinate) by using pictures taken from two or more directions, or by including a jig having a known coordinate in the image, to correct the occlusal contact positional data.

The obtainment method of the data of two-dimensional occlusal contact positional information (x, y) or three-dimensional occlusal contact positional information (x, y, z) where the occlusal contact positional distribution is emerged is not particularly limited, and a three-dimensional scanner may be exemplified.

Figure 2B:
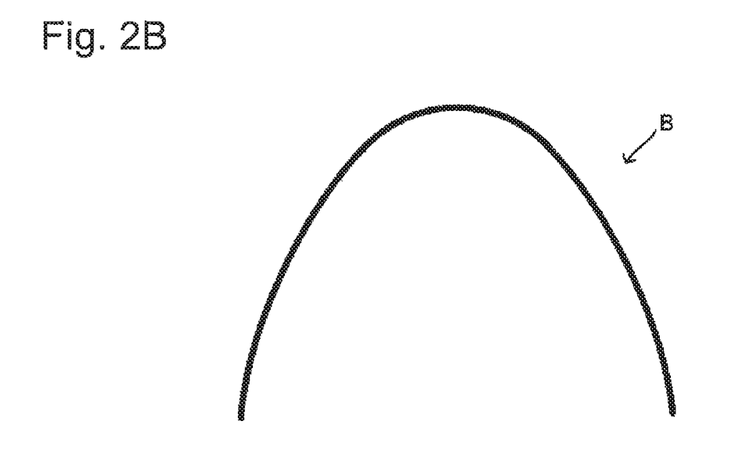

The step S14 is to calculate a formula B of a dental arch (formula B of a second dental arch) with occlusion pressure data as shown in FIG. 2B, from the distribution of information data of occlusion pressure generation points (x, y) among the occlusal contact positional data obtained by the step S13.

The calculation of the formula B can be made by calculation of the dental arch by regression analysis with the distribution of the occlusal contact positional data. Examples of the regression analysis include least square methods. It is preferred that the kind of the formula be the same as the formula A of the first dental arch calculated in the above step S12. That is, it is preferred that the formula B of the second dental arch be a formula of parabola when the formula A of the first dental arch is a formula of parabola, and that the formula B of the second dental arch be a formula of ellipse when the formula A of the first dental arch is a formula of ellipse. This makes it possible to increase transformation accuracy which is described later.

It is preferred that, when the occlusal contact positional information is three-dimensional, the formula of occlusal plain face or occlusal curved face as shown below be obtained by regression analysis etc. first, then the formula of dental arch projected to the plain face or curved face be obtained in the same way as in the two-dimensional way. Regarding the occlusal curved face, the formula may be decided based on theories such as Monson Spherical Theory and Spee Curve.

Formula of occlusal plain face:

$$D_1 x + D_2 y + D_3 z + D_4 = 0$$

Formula of occlusal curved face (spherical surface):

$$E_1 x^2 + E_2 x + E_3 y^2 + E_4 y + E_5 z^2 + E_6 z + E_7 = 0$$

Here, $D_1$ to $D_4$ and $E_1$ to $E_7$ are coefficients.

In this case as well, in view of easy analysis, not all of the occlusal contact positional data but only data of such as barycentric position of each occlusal contact area may be used for the regression analysis.

In the step S15, a transformation matrix to approximate the formula A of the first dental arch to the formula B of the second dental arch is obtained by operation. When the measurement of occlusion pressure is carried out with a pressure sensitive paper for example, the formula A of the first dental arch is considered to be different from the actual dental arch since the shape of the pressure sensitive paper is different when occlusion is made and when data is analyzed, as mentioned above. Therefore, the formula A of the first dental arch is transformed in the way to be approximated to the formula B of the second dental arch which is considered to be more similar to the actual dental arch.

As the transformation matrix $R_1$ when the positional data is three-dimensional, for example the following matrix may be exemplified. This is in the case where the occlusal contact positional information is three-dimensional (x, y, z), and $a_{11}$ to $a_{43}$ are coefficients.

$$R_1 * \begin{pmatrix} X \\ Y \\ 1 \end{pmatrix} = \begin{pmatrix} a_{11} & a_{12} & a_{13} \\ a_{21} & a_{22} & a_{23} \\ a_{31} & a_{32} & a_{33} \\ a_{41} & a_{42} & a_{43} \end{pmatrix} * \begin{pmatrix} X \\ Y \\ 1 \end{pmatrix} = \begin{pmatrix} x \\ y \\ z \\ 1 \end{pmatrix} \quad \text{[Formula 1]}$$

As the transformation matrix $R_2$ when the positional data is two-dimensional, for example the following matrix may be exemplified. This is in the case where the occlusal contact positional information is two-dimensional (x, y), and $b_{11}$ to $b_{33}$ are coefficients.

$$R_2 * \begin{pmatrix} X \\ Y \\ 1 \end{pmatrix} = \begin{pmatrix} b_{11} & b_{12} & b_{13} \\ b_{21} & b_{22} & b_{23} \\ b_{31} & b_{32} & b_{33} \end{pmatrix} * \begin{pmatrix} X \\ Y \\ 1 \end{pmatrix} = \begin{pmatrix} x \\ y \\ 1 \end{pmatrix} \quad \text{[Formula 2]}$$

Calculation of the coefficients $a_{11}$ to $a_{43}$ and $b_{11}$ to $b_{33}$ is not particularly limited, and for example they may be obtained in the following ways. Here, two examples are shown.

In one example, two or more characteristic points that the formulas A and B correspond to each other are extracted, and the above-mentioned coefficients are obtained from a system of equations with the points.

For example, considering the transformation matrix $R_2$ which is two-dimensional, when the formulas A and B are parabolas, the coefficients $b_{11}$ to $b_{33}$ that satisfy transformation equation are obtained with the coordinate values (X, Y, x, y) of the characteristic points such as the apex, focal point, directrix of each parabola by solving a system of equations.

On the other hand, when the formulas A and B are ellipses, the coefficients b11 to b33 that satisfy transformation equation are obtained with the coordinate values (X, Y, x, y) of the characteristic points such as the focal point, directrix, center, edge of major axis, edge of minor axis of each ellipse by solving a system of equations.

In this example, together with the above characteristic points, the point closest to the occlusion point positioned on the most distal side of each formulas A and B may also be used as a characteristic point. With this point, not only correction of the shape but also correction of scale may be carried out, which makes it possible to further increase the accuracy of the position of the final occlusion point.

In another example, affine transformation matrixes are obtained to be the transformation matrixes $R_1$ and $R_2$. That is, the affine transformation matrixes are obtained by specifying the rotation angle of the axis, magnification/reduction percentage of the axis, the positional shift of the origin of each of the quadric curved of the formulas A and B, to be the transformation matrixes $R_1$ and $R_2$.

It is noted in the step S15, after the calculation of the transformation matrixes of $R_1$ and $R_2$, fine adjustment may be manually allowed to the transformation matrixes of $R_1$ and $R_2$ with consideration of the condition of the actual row of teeth, based on the results of the calculation.

Figure 3:
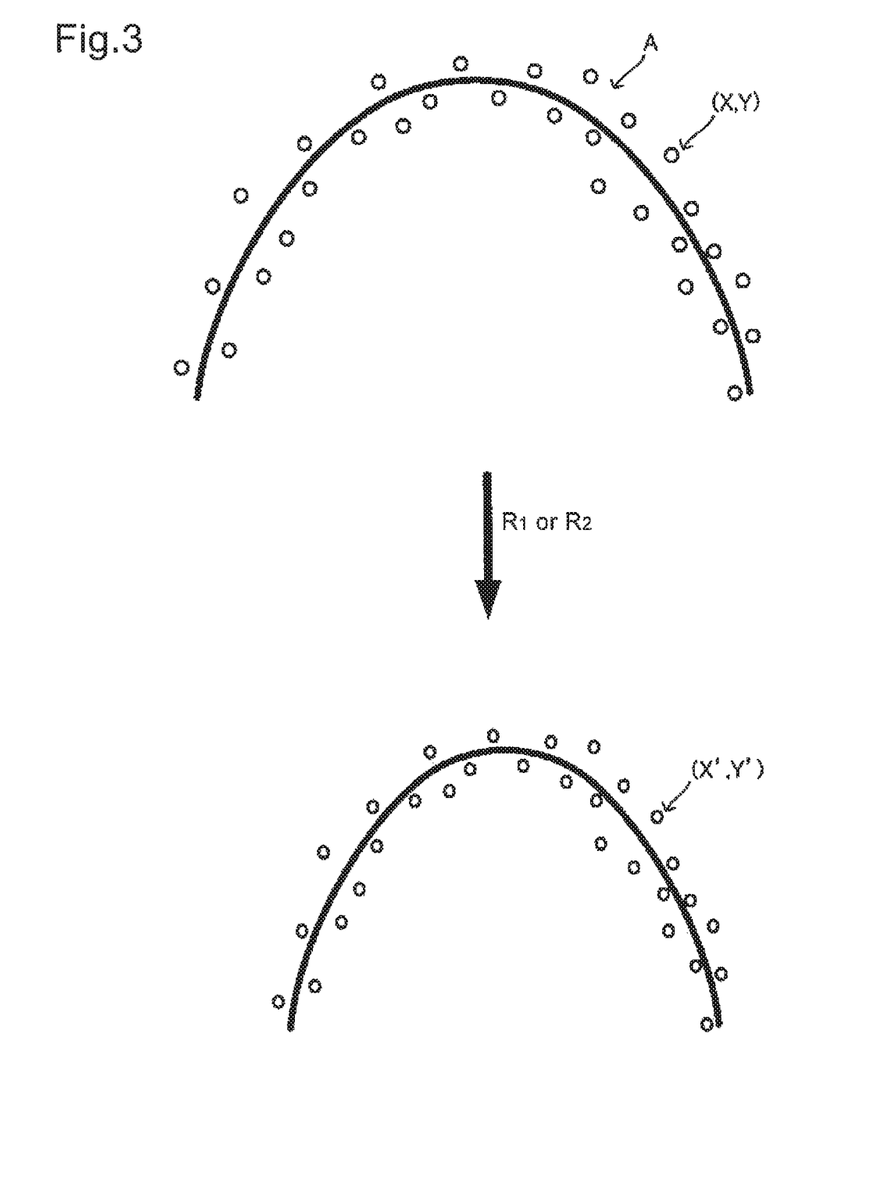
FIG. 3 is a view to explain that the positional information (X, Y) of occlusion pressure data is transformed by a transformation matrix to obtain a new positional information (X', Y').

In the step S16, as schematically shown in FIG. 3, the transformation matrixes $R_1$ and $R_2$ obtained by the step S15 are applied to each of the positional data of occlusion pressure obtained by the step S11 (data of coordinates (X, Y) shown by o in FIG. 3), to obtain occlusion pressure positional data after transformation (X', Y'). This new occlusion pressure positional data after transformation is transformed with the transformation matrixes $R_1$ and $R_2$. Thus, the data corresponds to the occlusal contact positional data with a good accuracy and shows the positions where occlusion pressure is made with a good accuracy.

This means that the occlusion pressure distribution is corrected to proper positions with a good accuracy with the data obtained by versatile methods (occlusion pressure data, occlusal contact positional data).

The occlusion pressure does not always occur at the all occlusion contact positions, which makes it difficult to individually coordinate the occlusion pressure data and occlusal contact positional data, and the coordination is very troublesome. Comparatively speaking, making transformation with the dental arch like the present embodiment easily makes the coordination with a good accuracy.

In the step S17, the occlusion pressure data ($P_{xy}$) among the above-described occlusion pressure data is added to the occlusion contact positional data. With the transformation of the positional information by the above transformation matrixes $R_1$ and $R_2$, the new occlusion pressure positions after transformation (X', Y') takes the same or similar value as the coordination of the occlusal contact positional data (x, y). Thus, the new occlusion pressure positional data obtained after transformation may be added to the coordination of the occlusal contact positional data as it is.

With this, the positions of the occlusion pressure and the occlusal contact positions are combined with a good accuracy.

It is noted that, after the occlusion pressure position after transformation (X', Y') is obtained, the agreement rate of the occlusion pressure position after transformation (X', Y') and the coordination of the occlusal contact positional data (x, y) is calculated, and if the agreement rate is low, the calculation may be carried out again with change of at least one of the formulas A, the formula B, the transformation matrix $R_1$, and the transformation matrix $R_2$. In this case, regarding the calculation of the agreement rate, it is preferred that the parameter be the data of the occlusion pressure position (X', Y') since the occlusion pressure does not always occur at the all occlusal contact positions.

In the step S18, the occlusion pressure including positional information obtained in the step S17 is overlaid with image of row of teeth to be shown. This makes it possible to visually see the positions where occlusion pressure is made and their sizes. As the image of row of teeth, the image used in the step S13 may be used for example.

According to the occlusion pressure analysis method S10 described above, it is possible to correct the occlusion pressure distribution to proper positions with a good accuracy with the data from information obtained from versatile methods, regardless of acquisition methods of the occlusion pressure and occlusal contact positional information which are sources of data.

By using this analysis result, it is possible to carry out occlusion pressure measurement at the accurate occlusion pressure positions.

It is noted that when the occlusion area is changed because of enlargement and contraction of the axis with the occlusion pressure position (X', Y') transformed with the transformation matrixes $R_1$, $R_2$, the correction may be made to show the area correctly and the correction of the value of the occlusion pressure may be made so that the value of occlusion power at occlusion points (occlusion area x occlusion pressure) becomes correct.

Figure 4:
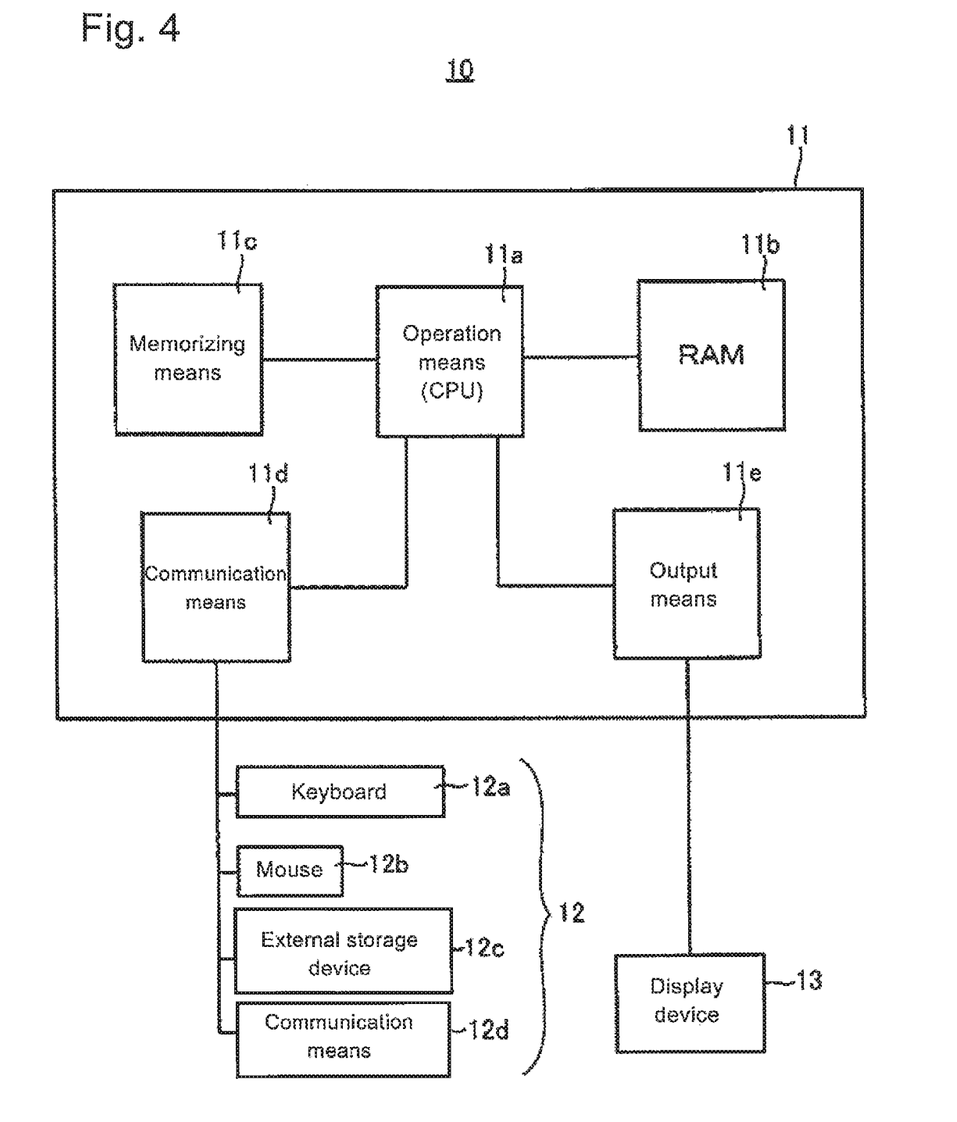
FIG. 4 is a view to explain the structure of a device for analyzing occlusion pressure 10.

Next, a device for analyzing occlusion pressure 10 according to one embodiment will be explained. FIG. 4 conceptually shows the structure of the device for analyzing occlusion pressure. The device for analyzing occlusion pressure 10 of the present embodiment includes an operation device 11, an input means 12, and a display device 13. The operation device 11 includes an operation means 11a, a RAM 11b, a memorizing means 11c, a receiving means 11d, and an output means 11e. The input means 12 includes a keyboard 12a, a mouse 12b, an external storage device 12c which functions as one storage media, and a communication means 12d.

The operation means 11a is formed from a so-called CPU (central processing unit), connected to each structural member, and can control the members. The operation means 11a also executes various programs stored in the memorizing means 11c etc. that function as a storage media, and functions as a means to carry out calculation included in the above occlusion pressure analysis method S10 and generation of various data based on the programs.

RAM 11b is a structural member functioning as a work area of the operation means 11a and a temporal data memorizing means. RAM 11b may be formed from SRAM, DRAM, flush memory, etc., and is same as known RAMs.

The memorizing means 11c is a structural member functioning as a storage media to save the above-described operation, various programs which are to be bases of the obtainment of data to be generated, and the data. Thus, as one of the programs, the storage means 11c storages a program including each step to execute the occlusion pressure analysis method S10. The memorizing means 11c may also storage various intermediate and final results obtained by the execution of the programs.

The receiving means 11d is a structural member having a function to properly take information from the outside into the operation device 11, to which the input means 12 is to be connected. A so-called input port, input connecter etc. are included in the receiving means 11d.

The output means 11e is a structural member having a function to properly output information that is to be output to the outside, among the obtained results, to which the display device 13 and various devices are to be connected. A so-called output port, output connecter etc. are included in the output means 11e.

The input device 12 includes the keyboard 12a, the mouse 12b, the outer storage device 12c, the transmitting means 12d etc. for example. A known keyboard and mouse may be used for the keyboard 12a and the mouse 12b and explanations thereof are omitted.

The outer storage means 12c is a known memorizing means that can make external connection and can also function as a storage media. Necessary various programs and data may be stored in the outer storage means 12c without particular limitation. For example, programs similar to the programs recorded in the above-described memorizing means 11c may be stored. As the outer storage device 12c, a known device may be used. The examples thereof include CD-ROM, CD-ROM drive, DVD, DVD drive, hard discs, various memories etc. The transmitting means 12d is a means to transmit data from another device to the receiving means 11d directly. The examples of the transmitting means 12d include the occlusion pressure detecting means shown in the step S13, a means to obtain occlusion pressure from the detecting means, and a device to obtain the occlusal contact positional data.

The display device 13 is a device to show operation results of each situation, selections of various functions etc. The operator operates the input means 12 referring to the display device 13 to make the operation device 11 function. As the display device 13, a known display device may be applied. For example, a monitor and the like may be used.

Examples of the operation device 11 include a computer. Normally the computer itself includes each device corresponding to the operation device 11, to which the input means 12 and the display device 13 may be connected.

According to the operation device 11 described above, based on the programs stored in the operation device 11 having each step to carry out the above steps S11 to S18, the occlusion pressure data and the occlusal contact positional data are input to the operation device 11 from the input means 12 as described in the steps S11 and S13, and the above-described operation of each step may be carried out by the operation device 11. Regardless of the acquisition method of the occlusion pressure and the occlusal contact positional information which are sources of data, it is possible to correct the occlusion pressure distribution to proper positions with a good accuracy by means of the data from information obtained by versatile methods.

The device for analyzing occlusion pressure that corrects the occlusion pressure distribution to proper positions with a good accuracy is explained here. This device may be configured to be incorporated in an occlusion pressure measurement device or an occlusal contact position measurement device to obtain occlusion pressure with the results by the device for analyzing occlusion pressure.

Alternatively, the device for analyzing occlusion pressure 10 may be configured to have at least one of the functions of occlusion power measurement, occlusion pressure measurement, and occlusal contact position measurement.

REFERENCES SIGN LIST 10 device for analyzing occlusion pressure
11 operation device
12 input means
13 display device

The invention claimed is:

1. A device for analyzing occlusion pressure comprising:
at least one memory storing program code; and
at least one hardware processor configured to execute the program code, the program code including:
  generating code configured to cause the at least one hardware processor to generate a formula of a first dental arch based on an occlusion pressure data, and generate a formula of a second dental arch based on an occlusal contact positional data, generate a transformation matrix that approximates the formula of the first dental arch to the formula of the second dental arch;
  transforming code configured to cause the at least one hardware processor to transform positional information included in the occlusion pressure data to a new positional information based on the transformation matrix; and
  output code configured to cause the at least one hardware processor to output, based on the transformation, an occlusion pressure data including the new positional information,
wherein outputting the occlusion pressure data including the new positional information comprises overlaying and displaying of the occlusion pressure data including the new positional information to an image of at least a row of teeth.

2. A non-transitory computer readable medium comprising instructions which, when executed, cause at least one hardware processor to analyze occlusion pressure by:
generating a formula of a first dental arch based on an occlusion pressure data;
generating a formula of a second dental arch based on an occlusal contact positional data;
generating a transformation matrix that approximates the formula of the first dental arch to the formula of the second dental arch; and
transforming positional information included in the occlusion pressure data to a new positional information based on the transformation matrix.

3. A method for analyzing occlusion pressure performed by at least one processor and comprising:
generating a formula of a first dental arch based on an occlusion pressure data;
generating a formula of a second dental arch based on an occlusal contact positional data;
generating a transformation matrix that approximates the formula of the first dental arch to the formula of the second dental arch; and
transforming positional information included in the occlusion pressure data to a new positional information based on the transformation matrix.

* * * * *